United States Patent
Pekarske et al.

(10) Patent No.: US 12,200,612 B2
(45) Date of Patent: Jan. 14, 2025

(54) METHODS AND SYSTEMS FOR CONDITIONAL SCANNING

(71) Applicant: GE Precision Healthcare LLC, Wauwatosa, WI (US)

(72) Inventors: Matthew Richard Pekarske, Grafton, WI (US); Tuomas Valtteri Laine, Vantaa (FI)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 402 days.

(21) Appl. No.: 17/648,269

(22) Filed: Jan. 18, 2022

(65) Prior Publication Data

US 2023/0232321 A1 Jul. 20, 2023

(51) Int. Cl.
*H04W 48/16* (2009.01)
*A61B 5/00* (2006.01)
*H04B 17/318* (2015.01)
*H04W 84/12* (2009.01)

(52) U.S. Cl.
CPC .......... *H04W 48/16* (2013.01); *A61B 5/0022* (2013.01); *H04B 17/318* (2015.01); *H04W 84/12* (2013.01)

(58) Field of Classification Search
CPC ..... H04W 48/16; H04W 84/12; H04W 48/20; A61B 5/0022; H04B 17/318; H04B 17/252; G16H 40/40; G16H 40/67
See application file for complete search history.

(56) References Cited

U.S. PATENT DOCUMENTS

| | | | | |
|---|---|---|---|---|
| 6,285,883 B1 * | 9/2001 | Bringby | ................ | H04W 36/30 370/332 |
| 9,426,724 B2 | 8/2016 | Parron et al. | | |
| 10,172,075 B1 * | 1/2019 | Singh | .................. | H04W 36/302 |
| 11,223,564 B2 | 1/2022 | Indiresan et al. | | |
| 2003/0069037 A1 * | 4/2003 | Kiyomoto | ............. | H04W 60/04 455/226.1 |
| 2004/0266474 A1 * | 12/2004 | Petrus | .................. | H04B 17/382 455/524 |
| 2008/0014934 A1 * | 1/2008 | Balasubramanian | ........................ | H04W 84/12 455/437 |
| 2008/0075035 A1 * | 3/2008 | Eichenberger | .... | H04W 36/0085 370/328 |
| 2008/0198811 A1 * | 8/2008 | Deshpande | ........... | H04W 48/16 370/332 |
| 2010/0303040 A1 * | 12/2010 | Takamune | ............ | H04W 48/16 370/331 |

(Continued)

OTHER PUBLICATIONS

Carvalho—An Enhanced Handover Oscillation Control Algorithm (Year: 2011).*

*Primary Examiner* — Fred A Casca
(74) *Attorney, Agent, or Firm* — McCoy Russell LLP

(57) ABSTRACT

Various methods and systems are provided for conditional scanning of a wireless network by a wireless monitoring system. The method for the wireless monitoring system comprises performing a scan of a wireless network in a first order to identify a plurality of access points (APs), reordering the plurality of APs to form a reordered group of APs based on a received signal strength indicator (RSSI) of each AP of the plurality of APs, and scanning the reordered group in a second order different than the first order to identify a candidate AP of the reordered group to roam to.

20 Claims, 5 Drawing Sheets

(56) References Cited

U.S. PATENT DOCUMENTS

| | | | |
|---|---|---|---|
| 2011/0216692 A1* | 9/2011 | Lundsgaard | H04W 48/20 370/328 |
| 2012/0230304 A1* | 9/2012 | Barbu | H04W 48/18 370/338 |
| 2012/0302176 A1* | 11/2012 | Cheng | H04W 48/16 455/67.11 |
| 2015/0038159 A1* | 2/2015 | Fang | H04W 48/16 455/452.2 |
| 2015/0173122 A1* | 6/2015 | Schliwa-Bertling | H04W 52/0235 370/311 |
| 2016/0183181 A1* | 6/2016 | Lee | H04W 48/16 370/338 |
| 2018/0070295 A1* | 3/2018 | Henry | H04W 36/00835 |
| 2018/0160364 A1* | 6/2018 | Wang | H04W 24/10 |
| 2019/0373539 A1* | 12/2019 | Chen | H04W 48/16 |
| 2020/0021996 A1* | 1/2020 | Harrod | H04W 16/10 |
| 2020/0077324 A1* | 3/2020 | Choi | H04M 15/8044 |
| 2020/0252851 A1* | 8/2020 | Tukmanov | G05D 1/0212 |
| 2021/0112427 A1* | 4/2021 | Shveki | G06T 19/006 |

* cited by examiner

METHODS AND SYSTEMS FOR CONDITIONAL SCANNING

FIELD

Embodiments of the subject matter disclosed herein relate to wireless monitoring systems.

BACKGROUND

Wireless network systems may be used in retail, industry, medicine, manufacturing, and other enterprise environments to transmit and receive information among elements of a wireless network. For example, handheld devices or other wireless monitoring systems may be wirelessly connected to a network via a plurality of access points (AP) of the wireless network system. Information such as inventory, machine availability, part manufacturing progress, and so on may be transmitted from the handheld device to the network via APs such that information input or stored on the handheld device may be accessed by other devices connected to the network. As the handheld devices move about a physical space of the wireless network system, a signal strength between an AP connected to the handheld device and the handheld device may change, for example, as the handheld device moves closer to or further from the connected AP. The signal strength may affect a speed of information transmission, energy used for transmission, and a time between information transmission by the handheld device and information receipt by the network. Thus, it may be desirable to roam to a different AP of the plurality of APs to maintain or improve a wireless connection strength between the handheld device and the network.

BRIEF DESCRIPTION

In one embodiment, a method comprises performing a scan of a wireless network in a first order to identify a plurality of access points (APs), reordering the plurality of APs to form a reordered group of APs based on a received signal strength indicator (RSSI) of each AP of the plurality of APs, and scanning the reordered group in a second order different than the first order to identify a candidate AP of the reordered group to roam to.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be further explained in the following description of non-limiting embodiments, with reference to the attached drawings, wherein below.

DETAILED DESCRIPTION

The following description relates to various embodiments of a system and methods for conditional scanning of a network by a wireless monitoring system, such as a Wi-Fi station (STA). In the herein described embodiment, the Wi-Fi STA is also referred to as a patient monitor, which may be used to transmit patient physiological data. The methods described herein may be applied to other enterprise environments, including retail, industry, manufacturing, and so on, where wireless network systems may be used to transmit and receive information among elements of a wireless network.

In a hospital or other medical setting, monitoring of a patient's physiological information may be done in part using mobile patient monitors or other mobile medical devices. A patient monitor may monitor a patient as the patient, and therefore the patient monitor, moves about a space such as the patient's room or the hospital. The patient monitor may be connected to at least one of a plurality of APs. The plurality of APs are connected to a network, which may further include a patient information database and/or other devices by which medical professionals may access and monitor patient data.

As the patient and therefore the patient monitor moves about a space, an available wireless signal strength may change. It may be desirable to roam to a different AP of the plurality of APs (e.g., switch from a connected AP to a different AP) to maintain or improve a wireless connection strength between the patient monitor and the network. Devices in a healthcare setting may roam when stationary, due to changing environment (e.g., Wi-Fi Infrastructure events such as channel or power level changes, and/or a room door opening or closing), or when the patient monitor is mobile. Stationary roaming events may occur on the order of a few an hour whereas mobile events may occur once per 30 seconds for a duration of 15 minutes several times a day when the patient monitor is mobile, for example, when the patient walks a lap around the ward or goes to the cafeteria. Stationary and mobile roaming events may allow the patient monitor to disconnect from a currently connected AP and connect to a candidate AP in the space which may have a stronger wireless signal, thus allowing for continued transmission of information from the patient monitor to the network when the patient monitor is mobile or during environmental changes.

Figure 1:
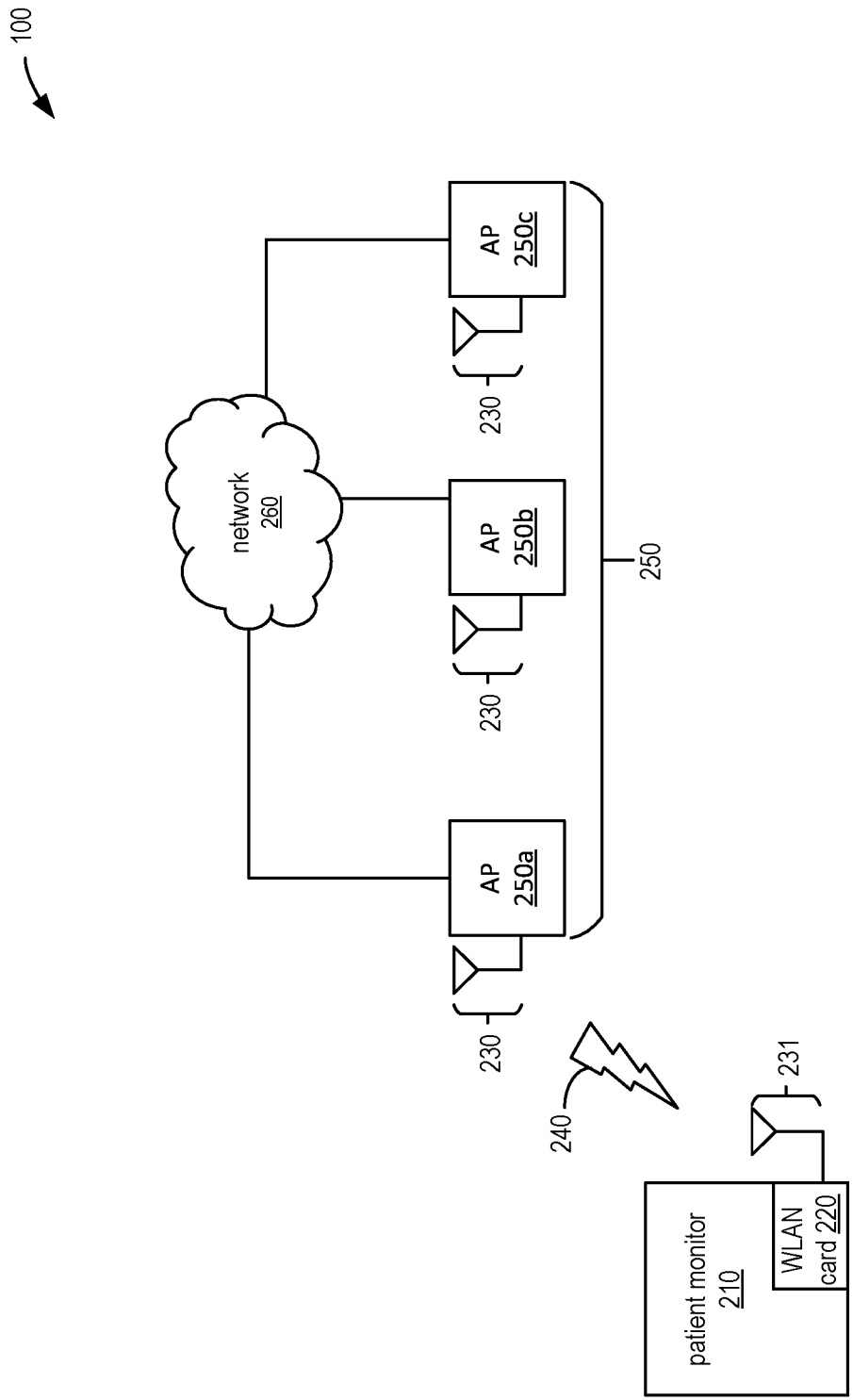
FIG. 1 shows a schematic block diagram illustrating communication of a Wi-Fi station (STA) with a plurality of access points (APs).

An example wireless system, as shown in FIG. 1, includes at least one patient monitor and a plurality of access points (APs). The APs are connected to a network and may be in wireless communication with the patient monitor via wireless transmission. For example, the patient monitor may be in wireless communication with a current AP of the network and may roam to a candidate AP of the network when roaming is triggered, as further described in FIG. 2.

The patient monitor may include a WLAN wireless card, which may store and execute computer executable code. For example, the code may include a method for conditional scanning of the network. Conditional scanning, as described in a high-level flow chart in FIG. 3, may include performing a full scan, reordering full scan results, adjusting a hysteresis value, and executing subsequent scans (e.g., a full scan or a reordered scan) on a reordered group of the plurality of APs.

The reordered scan may include filtering full scan results shown in the reordered group based on a received signal strength indicator (RSSI) of the candidate AP relative to an RSSI of the current AP and a hysteresis value. The hysteresis value may be a threshold used to determine whether an RSSI of the candidate AP is different enough from the RSSI of the connected AP (e.g., in wireless communication with the patient monitor) to potentially have a stronger wireless connection with the patient monitor. The hysteresis value may be adjusted prior to execution of the reordered scan to allow more or less aggressive roaming of the patient monitor, as further described in FIG. 4.

Figure 5:
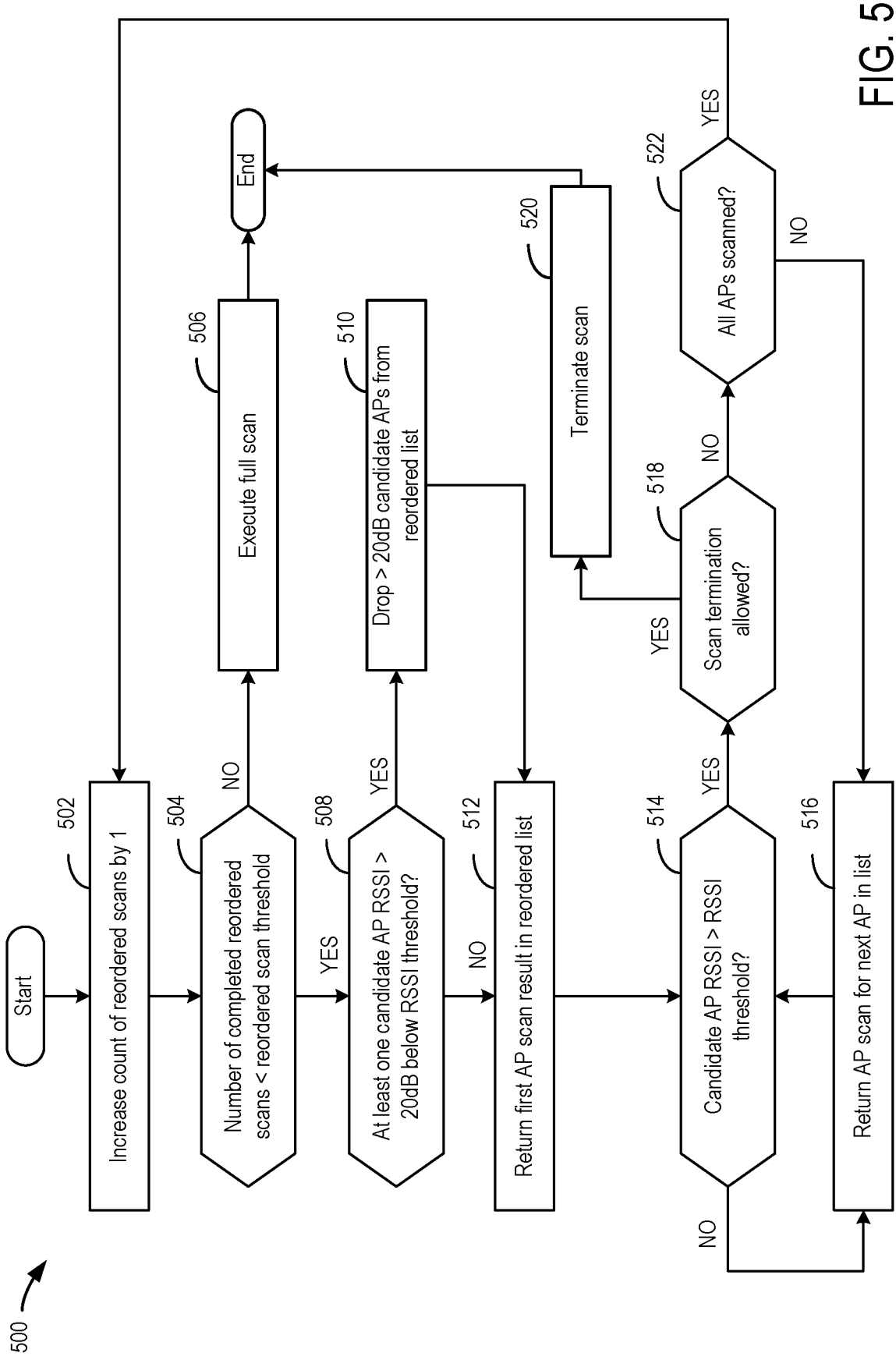
FIG. 5 shows a flow chart illustrating a method for determining whether to implement a reordered scan or a full scan of the network.

Details of a method for executing a subsequent scan (e.g., the full scan or the reordered scan) on the reordered group are shown in FIG. 5, which may be done following adjustment of the hysteresis value. Implementing the reordered scan may result in a decreased roaming response time, decreased data loss during roaming, and decreased power draw during scanning of the network compared to the full scan.

Before further discussion of the method for conditional scanning of the network, an example system in which the method may be implemented is shown. FIG. 1 shows one embodiment of a schematic block diagram illustrating communication of a patient monitor with a plurality of access points (APs).

In operation, a system 100 includes a patient monitor 210 which is in communication through a wireless transmission 240 to a first AP 250a of a plurality of APs 250. Herein, the first AP 250a may also be referred to as the connected AP. An AP in wireless communication with the patient monitor 210 such that data may be transmitted may also herein be referred to as "the connected AP". Physiological information collected by the patient monitor 210 is relayed through the first AP 250a to a network 260. The system 100 uses a WLAN card 220 and a transmitter/transceiver 231 associated with the patient monitor 210 and each of a transmitter/transceiver 230 associated with an AP of the plurality of APs 250 to facilitate the wireless transmission 240 of physiological data.

The system 100 includes the patient monitor 210 having the WLAN card 220 (e.g., a wireless card) and the transmitter/transceiver 231. The plurality of APs 250, each having a transmitter/transceiver 230, are dispersed throughout a physical space, for example, a hospital or other healthcare facility. For example, the first AP 250a, a second AP 250b, and a third AP 250c each have an associated transmitter/transceiver 230. The plurality of APs 250 are thus dispersed throughout a physical space of the wireless network and are connected through the network 260. In one example, the patient monitor 210 and each of the plurality of APs 250 may have a separate transmitter and transceiver. As described herein, the transmitter/transceiver is a single device with transmitting and receiving capabilities.

The patient monitor 210 may be any patient monitoring device with wireless monitoring capabilities. For example, the patient monitor 210 may be a Wi-Fi station (STA). In one embodiment, the WLAN card 220 is an original equipment manufacturer (OEM) card and includes a storage medium having computer executable code and a processor to execute the code. The WLAN card 220 may thus implement the method for conditional scanning of the network, as further described herein. In further embodiments, the patient monitor 210 includes a storage medium and a processor which are not part of the WLAN card 220 and operate to store and execute computer executable code respectively, otherwise stored on and executed by the WLAN card 220. Additional embodiments of the system 100 may include a patient monitor 210 without a WLAN card 220 and the patient monitor 210 may instead have hardwired circuitry and executable code incorporated directly therein.

The plurality of APs 250 are connected through the network 260. For example, the system 100 may include a number of APs 250 connected to the network 260. The plurality of APs 250 may be configured throughout the area of the system 100 to monitor a number of patient monitors 210, which are also configured throughout the system 100 and placed in close proximity to a patient being monitored. In the example described herein, the system 100 is a wireless system and patient monitors within the system 100 may be mobile. For example, the patient monitors may monitor patients as the patients, and therefore the patient monitors, move about a space such as the patients' room or the hospital. The patient monitor 210 and the plurality of APs 250 are communicatively coupled via the wireless transmission 240 generated by the patient monitor's transmitter/transceiver 231 and one or more transmitters/transceivers 230 belonging to the APs 250, as further described in FIG. 2. The network 260 receives wirelessly transmitted information from the APs 250 and relays the information collected from the APs 250 to a hospital information system suitable for collecting and managing such information. Such hospital information systems are known in the art and the present system 100 is adaptable to different hospital information systems.

Once the patient monitor 210 is in wireless transmission 240 with the first AP 250a, the WLAN card 220 conducts a scan of the system 100 to determine if another of the APs 250 (e.g., the second AP 250b or the third AP 250c) may have a stronger signal quality than the first AP 250a the patient monitor 210 is currently in communication with. As described above, current system may use the signal strength of access points 250 to determine whether to enter a roaming mode, thus allowing the patient monitor 210 to connect with a second AP (e.g., a candidate AP) and drop the first AP (e.g., the connected AP). The method for triggering roaming, scanning the network, selecting an AP of the plurality of APs, and roaming to a selected AP is further elaborated on in FIGS. 2-5.

When a Wi-Fi STA is in a degraded signal condition or in a congested wireless network (e.g., many devices attempting to connect to the network via the plurality of APs), it is desirable for the Wi-Fi STA to roam to (e.g., seek out and connect to) a candidate AP with a greater RSSI than an RSSI of a connected AP. It is desirable that this is accomplished in a timely manner such that application performance (e.g., monitoring of a patient's physiological information) is not degraded.

A roaming process may include four main categories: trigger, scan, select, and roam. In the trigger phase, the Wi-Fi STA measures a wireless environment it is positioned in and compares measured data to defined roaming trigger thresholds, as further described herein. For example, the Wi-Fi STA measures an RSSI of the connected AP to determine if the RSSI of the connected AP is less than a roaming trigger threshold. In one example, a 'high' RSSI value may be greater than −50 dBm and RSSI values less than −80 dBm may be 'low'. Thus, the roaming trigger threshold may be a value such that, when the RSSI of the connected AP is less than the roaming trigger threshold, the Wi-Fi STA enters a scan phase to identify available APs in the wireless network (e.g., identifies a plurality of candidate APs). Upon completion of the network scan, the Wi-Fi STA enters a select phase where the Wi-Fi STA determines which of the plurality of APs to connect to. Once the Wi-Fi STA selects a candidate AP to roam to, the Wi-Fi STA enters a roam phase, where the Wi-Fi STA authenticates and associates with the candidate AP based on AP characteristics described below. All of the above phases are completed prior to the Wi-Fi STA being able to send its intended application data to the network via the connected AP.

Of the four areas above, and assuming that the roaming trigger thresholds are established correctly (e.g., during setup of a network and/or programming of the Wi-Fi STA), roaming delay may occur in the scan phase followed by the roam phase, depending on the complexity of the security method used in the Wi-Fi STA. Roaming delay, or an interruption in application data, is defined as a duration between the last data packet transmitted to a first AP (e.g., the connected AP the Wi-Fi STA was previously connected to) and the first data packet transmitted to a second (e.g., candidate) AP. Roaming delay may increase a roaming response time, increase data loss, and increase power draw due to excessive scanning.

Figure 2:
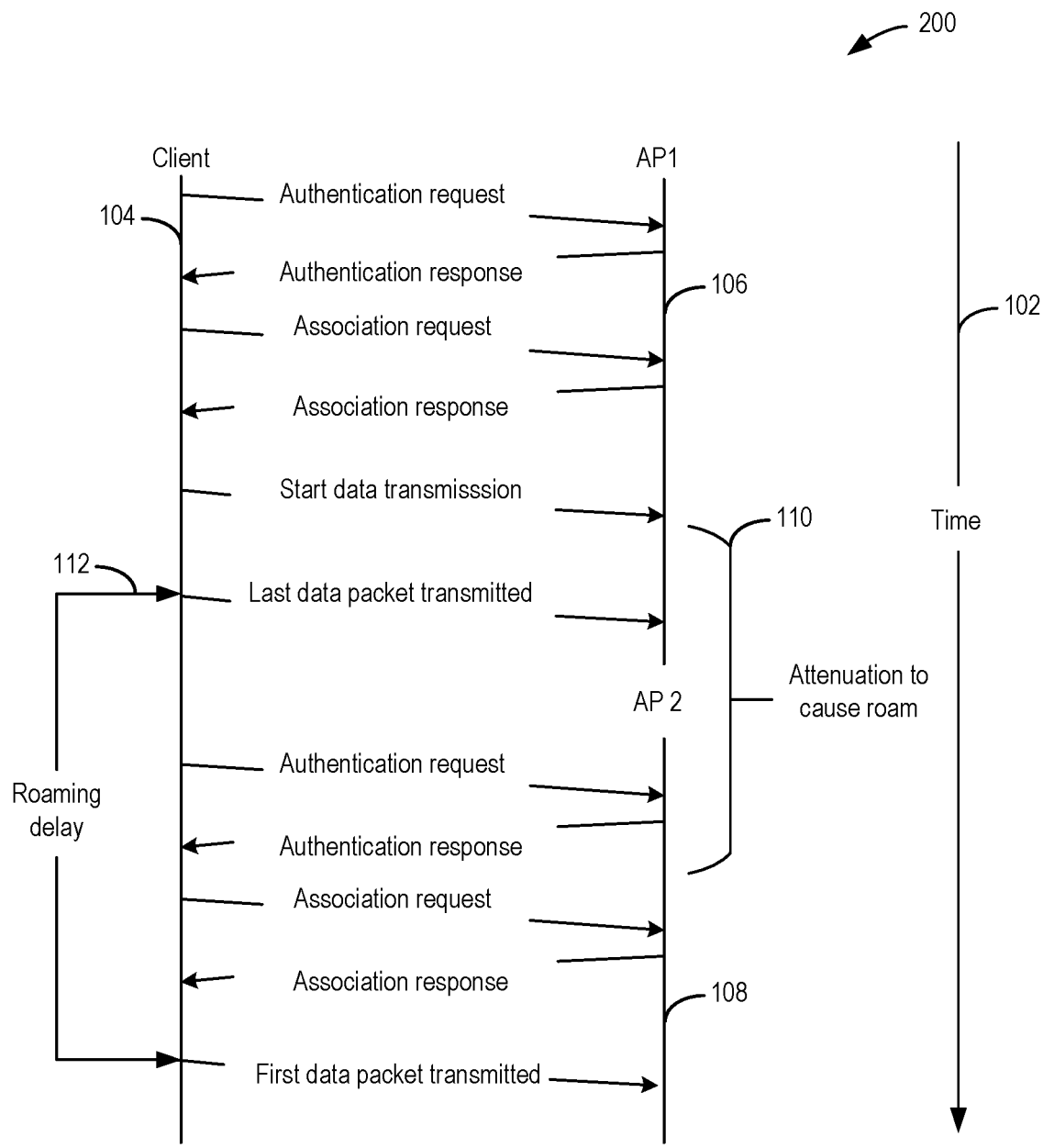
FIG. 2 shows a timeline illustration of roaming delay for a client.

FIG. 2 shows a timeline illustration 200 of roaming delay for a client. Time increases as shown by arrow 102. The client 104 may be a Wi-Fi STA or other mobile monitoring device which may be wirelessly connected to a network via an AP. The client 104 is initially connected to a first AP (AP1) 106. During the roam phase, the client 104 sends an authentication request to the AP1 106, and the AP1 106 sends an authentication response to the client 104. The client 104 then sends an association request to the AP1 106, and the AP1 106 sends an association response to the client 104. In response to the association response from the AP1 106, the client 104 starts data transmission to the AP1 106. Transmitted data may include patient physiological information such as heart rate, blood pressure, and so on. The AP1 106 may thus be considered a connected AP, as the client 104 may be in wireless communication with the network via the AP1 106.

The roaming process for the client 104 (e.g., Wi-Fi STA) begins following one or more of its roaming trigger thresholds being exceeded. Depending on how configurable the client 104 driver/firmware is, any number of a plurality of parameters may be used for the roaming trigger threshold. The parameters may include RSSI, signal-to-noise ratio (SNR), data retries in a given time period, number of expected beacons not received in a given time period, current data rate, and time since last scan. RSSI is the parameter most commonly used, however, in a wireless environment where wireless interference or high client loading is anticipated, additional roaming trigger thresholds may be considered. For example, if the AP1 106 has a high RSSI value, but the client 104 is operating on a channel that is being interfered with, the noise floor may be higher than normal and/or the data retries may increase. Therefore, a combination of RSSI, SNR, and data retries may be used to trigger the client to roam in higher interference scenarios as well as low signal conditions.

In the example of FIG. 2, roaming is triggered by a loss of signal strength or by a degradation of signal strength (e.g., as determined by a RSSI of the connected AP) below the roaming trigger threshold in a networking connection. For example, the wireless connection between the client 104 and the AP1 106 may be degraded when the client 104 is mobile (e.g., moving away from the AP1 106) or when a physical environment of the network changes (e.g., a door opens/closes). It may be desired for the client 104 to roam to a different AP, for example, a second AP (AP2) 108.

After one or more roaming trigger thresholds have been exceeded, the client 104 may scan available channels (e.g., APs) to potentially roam to. The client 104 may use active scanning or passive scanning to identify a candidate AP. Active scanning includes the client 104 sending out probe requests (e.g., authentication requests) on the channels it is not currently connected to and listening for a first duration (e.g., 10 to 50 ms) for a probe response (e.g., authentication response) from the AP. Passive scanning includes the client 104 listening for beacons from APs in the wireless environment. Beacons may be broadcast at a first frequency, for example, one beacon may be emitted by an AP per 100 ms. The client 104 may thus listen for beacons for 1.5 times the beacon rate (e.g., 150 ms) so as to not miss a present beacon. Active channel scans may be completed faster than passive channel scans. In one example, Wi-Fi STAs operating in an 802.11a band may use dynamic frequency selection (DFS) to scan available channels. DFS may reduce interference with radar systems that operate on the same channels. Therefore, passive scans may be used on UNII-2 and UNII-Worldwide bands.

In the 802.11b/g (2.4 GHz) band, there are between 11 and 14 channels available for use depending on the domain the Wi-Fi STA is operating in (FCC vs. ETSI). In the 802.11a (5 GHz) band, there are up to 23 channels available. If passive scans are done to completion on all 14 802.11b/g and 23 802.11a channels, with a scan delay of 150 ms per channel, scanning alone could amount to 5.5 seconds. With Wi-Fi 6E adding up to 59 additional channels, scanning times increases.

Once the client 104 has completed the scanning process, it selects a candidate AP to connect to. The candidate AP may have a greater RSSI and/or a higher SNR (e.g., greater signal than noise) compared to the AP the Wi-Fi STA is currently connected to (e.g., the AP1 106). When multiple APs are available in the wireless network which the Wi-Fi STA may roam to, multiple parameters may be considered to determine which AP to roam to. Parameters may include RSSI, SNR, data retries in a given time period, number of expected beacons not received in a given time period, current data rate, time since last scan, and AP client loading. Parameters may further include a difference between values of the aforementioned parameters for the AP in question compared to the connected AP.

The above-mentioned parameters are similar to those used as roaming trigger thresholds, with the exception of AP client loading and hysteresis. For example, if only RSSI is used to sort candidate APs and the RSSI of an AP having the highest RSSI of the candidate APs is 2 dB greater than the connected AP RSSI level, then roaming to the candidate AP may result in more drawbacks than benefits. For example, roaming to the candidate AP having an RSSI 2 dB greater than the connected AP induces interruption of application data transmission and is likely to cause another scanning process, as the 2 dB difference may not be a significant increase in signal strength.

The inclusion of additional parameters, such as hysteresis, may help make the scanning and roaming steps more selective. The hysteresis value selection process weighs a desire for connection to an AP with a highest connected data rate of the candidate APs and lowest interruption of application data as is tolerable by the Wi-Fi STA. Table 1 below is an example guide for a designer in selecting a hysteresis value that makes the Wi-Fi STA more aggressive (e.g., less sticky, or more likely to change between APs) or less aggressive (e.g., more sticky, or less likely to change between APs) when deciding to roam from its connected AP. Further details regarding adjustment of the hysteresis value are described in FIG. 4.

TABLE 1

Hysteresis Guide

| Factor | More "Sticky" | Less "Sticky" |
|---|---|---|
| # of APs for size of facility | Few | More |
| Mobility of Wi-Fi STA | Low | High |
| Bandwidth Utilization | Small | Large |
| Application persistence request | High | Low |

As described above, the client 104 may scan the network to identify a plurality of candidate APs. The client 104 may select the AP2 108 as a candidate AP. In the example of FIG. 2, which may use IEEE 802.11 protocol, the client 104 first disconnects from the connected AP (e.g., the AP1 106). The client 104 then switches to the candidate AP (e.g., the AP2 108), reauthenticates, reassociates, potentially pulls a new IP address (e.g., for layer three roams), all prior to being able to resume sending application data.

For example, the client 104 sends an authentication request to the AP2 108, and the AP2 108 sends an authentication response to the client 104. A first duration 110 may be a time in which attenuation occurs, thus causing the client 104 to roam to the second AP. In the example of FIG. 2, the first duration 110 is between the start of data transmission from the client 104 to the AP1 106 and when the client 104 receives the authentication response from the AP2 108. As was done when connecting the client 104 to the AP1 106, the client 104 sends an association request to the AP2 108 following receipt of the authentication response. The AP2 108 sends an association response to the client 104, and a first data packet is transmitted from the client 104 to the AP2 108.

A roaming delay 112 is the duration between when the last data packet was transmitted from the client 104 to the AP1 106 and when the first data packet is transmitted from the client 104 to the AP2 108. During the roaming delay 112, data (e.g., patient information) may not be transmitted to an AP and therefore not communicated to the network. Medical providers may thus be unable to monitor patients using information gathered by the client 104 for the duration of the roaming delay 112.

In the aforementioned example, infrastructure based methods (e.g., IEEE 802.11k, v) manipulate Wi-Fi STA roaming behavior based on Wi-Fi STA performance from the AP's perspective. However, the AP-based methods may miss near-far scenarios where the AP can hear its neighbors and connected STAs (e.g., can detect RSSI and other characteristics listed above), but the Wi-Fi STA itself may be unable to detect a plurality of candidate APs.

A current wpa_supplicant, used for key negotiation with an authenticator on the network infrastructure, controlling roaming behavior and IEEE 802.11 authentication/association of the wireless driver, supports two methods for detecting available APs. A bgscan simple method scans all pre-programmed channels in an array in the same order when a scan request is initiated. If a mobile STA is not in a location where it can hear an AP on a channel listed in the channel array, the wpa_supplicant will still spend 50-150 ms per channel listening for the transmissions from an AP on that channel. The more channels that a STA cannot hear, the more time the STA may take to find a channel deemed a sufficient roaming candidate. Further complicating matters is the release of new spectrum for Wi-Fi 6E in the 6-7 GHz frequency band which will greatly increase the number of channels the STA has potentially available to scan. Conversely, a bgscan learn method scans all channels observed during a previous scan plus one new frequency that was not previously heard during scanning. This method reduces the channel set to what the STA hears in a given location. However, when the STA moves, a potentially entirely new channel list may be desired to capture APs in the new location. Since bgscan learn scans one new channel in addition to the ones it already knows from the previous location, there would be an increased probability of the STA missing available channels as it moves to the new location as subsequent scans might not scan all available channels before the STA moves past a candidate AP.

Both methods scan for channels based on a static, pre-programmed configuration. In other words, the channel scan list is not updated (e.g., add/remove channels) or reordered dynamically based on changing conditions observed by the STA. The process for a Wi-Fi STA to determine optimal APs to connect to as described above may result in a slow roaming response, increased data loss and increased power draw due to excessive scanning when the Wi-Fi STA is mobile. A method having advantages of both the bgscan simple method and bgscan learn method is desired to optimize roaming performance for Wi-Fi STAs that have Wi-Fi PHY/MAC radios reliant on a host processor running an OS as well as self-contained Wi-Fi radios running their own OS. In one example, roaming delay may be reduced by adjusting at least one of: support for multiple trigger parameters (e.g., RSSI and SNR), pre-emptive scanning, hysteresis, and authentication.

As briefly described above, FIG. 3 illustrates a method for conditional scanning of a network by a Wi-Fi STA. Conditional scanning may include implementation of either a full scan or a reordered scan, where the reordered scan may be used to reduce data loss and reduce power draw during roaming of the Wi-Fi STA. Conditional scanning may include performing a full scan, reordering results of the full scan (e.g., a plurality of APs) based on an RSSI of each of the plurality of APs, adjusting a hysteresis value, and executing a subsequent scan (e.g., a full scan or a reordered scan) on a reordered group of the plurality of APs. Implementing a reordered scan may decrease a roaming delay of the Wi-Fi STA and allow the Wi-Fi STA to roam to an AP with a greater RSSI, thus reducing data loss and reducing power draw during roaming. Further detail of adjusting the hysteresis value is described in FIG. 4, and detail of executing subsequent scans on the reordered group is described in FIG. 5.

As described above, a roaming method may be implemented when a roaming trigger threshold is exceeded. The Wi-Fi STA then scans the network to identify a plurality of candidate APs to which the Wi-Fi STA may roam. In the herein described method, the Wi-Fi STA may perform a full scan or a reordered scan. In one example, the reordered scan may be performed based on a reordered scan threshold, where the full scan is executed when the number of completed reordered scans is equal to or exceeds the reordered scan threshold. In another example, the WLAN card may include computer-readable instructions for determine a frequency at which to implement a full scan based on environmental conditions, for example, how often the roaming trigger threshold is exceeded, how often the Wi-Fi STA roams to a new AP when a scan is implemented, and so on.

Further detail regarding whether a full scan or a reordered scan is performed is described in FIG. 5.

Figure 3:
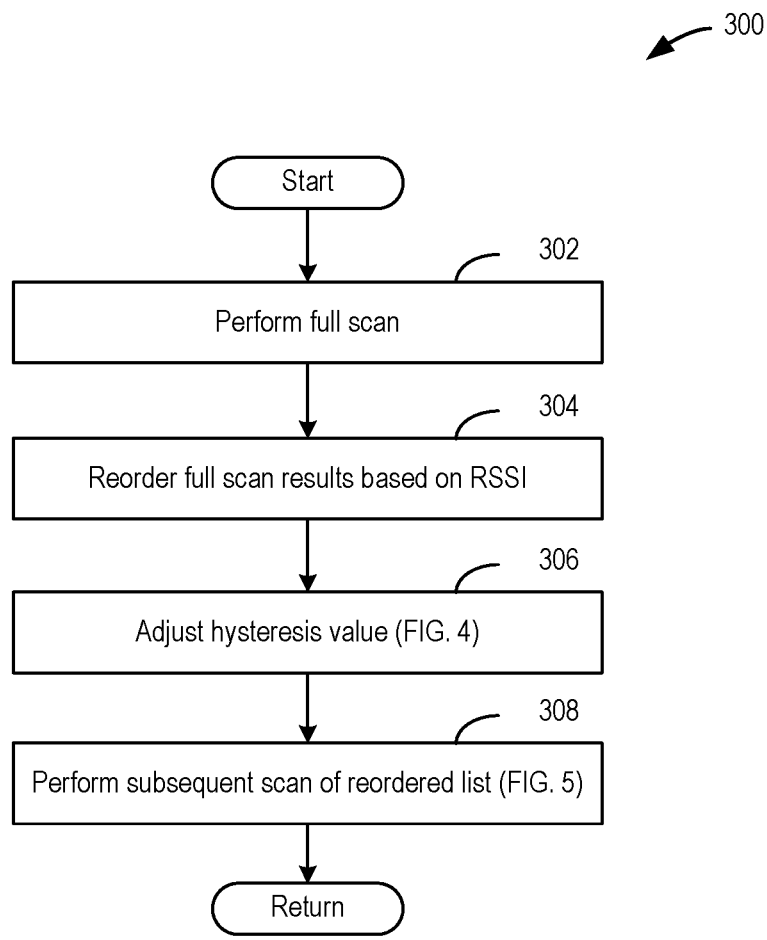
FIG. 3 shows a flow chart illustrating a high-level method for conditional scanning of a network by a Wi-Fi STA.

A method 300 illustrated in FIG. 3 may be implemented when a roaming trigger threshold, as described above, is exceeded, and the Wi-Fi STA implements a conditional scan. In some embodiments, the method 300 and other methods described herein may be computer-readable instructions executed by the WLAN card 220 of the patient monitor 210 of FIG. 1. The method 300 and other methods described herein are described with reference to the wireless network system of FIG. 1, and may be applied to other embodiments of wireless network systems including at least two APs and a mobile patient monitoring device. In one example, as described in the method 300 of FIG. 3, implementing a conditional scan may include performing a full scan, reordering scan results, adjusting a hysteresis value, and executing subsequent scans (e.g., a reordered scan or a full scan) on the reordered group.

At 302, a full scan is performed, where the Wi-Fi STA scans each channel of the network in a first order to identify a plurality of candidate APs. Beacons may be broadcast from an AP at a first frequency. In one embodiment, the first frequency is one beacon per 100 ms. The Wi-Fi STA records the RSSI of each of a plurality of beacons it receives from a given AP. The RSSI is the signal strength of the beacon as it is received by the STA. In other words, the RSSI is a power level that the STA observes of the received beacon. The Wi-Fi STA may, in one example, average the RSSI of a plurality of beacons (e.g., 5-10 beacons) for the given AP to determine the RSSI value for the AP. In another example, the Wi-Fi STA may record the RSSI of the first beacon of the given AP.

Operation 302 may further include determining RSSI values of a connected AP (e.g., an AP currently connected to the Wi-Fi STA). When the Wi-Fi STA is mobile or a surrounding environment is changing, a strength of a signal (e.g., wireless transmission) between the Wi-Fi STA and the connected AP may change, as indicated by a changing RSSI.

At 304, the method 300 includes reordering the plurality of APs. In one example, the plurality of APs are stored as a list. As an alternative example, the plurality of APs may be stored as multiple groupings of information which are not listed in a specific order. In the present embodiment, the plurality of APs are arranged in a list stored on the WLAN card. For example, during the full network scan, the plurality of APs may be listed in the order which RSSI values from a respective AP were collected. The list may be reordered in order of ascending RSSI values, such that an AP of the plurality of APs with the highest RSSI value is at the top of a reordered list and therefore, is the first AP scanned by the Wi-Fi STA during adjustment of the hysteresis value and a subsequent scan of the reordered list. In one example, the full scan may return the plurality of APs in the first order, such as: a first AP with an RSSI of −65 dBm, a second AP with an RSSI of −75 dBm, and so on through a $n^{th}$ AP with an RSSI of −50 dBm. Following reordering, a subsequent scan is performed on the plurality of APs in a second order, different from the first order, as described in FIG. 5. For example, the second order is: the $n^{th}$ AP with the RSSI of −50 dBm, the first AP with the RSSI of −65 dBm, and so on in order of descending RSSIs through the second AP with the RSSI of −75 dBm, where the second AP has the smallest RSSI of the plurality of APs.

At 306, the method 300 includes adjusting a hysteresis value. For example, the hysteresis value may be increased or decreased, based on the RSSI of the current AP and the RSSIs of a first three candidate APs on the reordered list. The hysteresis value used to determine a threshold value (e.g., signal strength) for roaming from the connected AP to a candidate AP (e.g., an AP of the plurality of APs) may be set to a large value when the Wi-Fi STA is stationary to avoid flip-flopping (e.g., rapidly roaming back and forth) between two APs of similar RSSI. Alternatively, the hysteresis value may be adjusted to a lower value when the Wi-Fi STA is mobile to allow the Wi-Fi STA to be more aggressive in roaming to a new AP that it is headed toward. Furthermore, if the Wi-Fi STA was far away from any candidate APs, the hysteresis value could be adjusted even lower to allow the Wi-Fi STA to connect to any candidate AP that with a slightly higher signal strength to increase the probability of not losing connection entirely. As the hysteresis value indicates a relative quantity, the hysteresis value uses units of dB. Discussion of absolute values (e.g., RSSI values) uses units of dBm. Further detail regarding adjustment of the hysteresis value is described in FIG. 4.

At 308, the method 300 includes executing a subsequent scan of the reordered list to identify which of the plurality of APs may be selected as the candidate AP to which the Wi-Fi STA may roam to increase a wireless connection strength between the Wi-Fi STA and the network. The subsequent scan may be either a full scan or a reordered scan. Further detail regarding execution of subsequent scans is described in FIG. 5.

Following the subsequent scan of the reordered list, the Wi-Fi STA may remain connected to the connected AP or may roam to a new AP of the plurality of APs. As described above, conditional scanning (e.g., the method 300) may be repeated when the roaming trigger threshold is exceeded.

Figure 4:
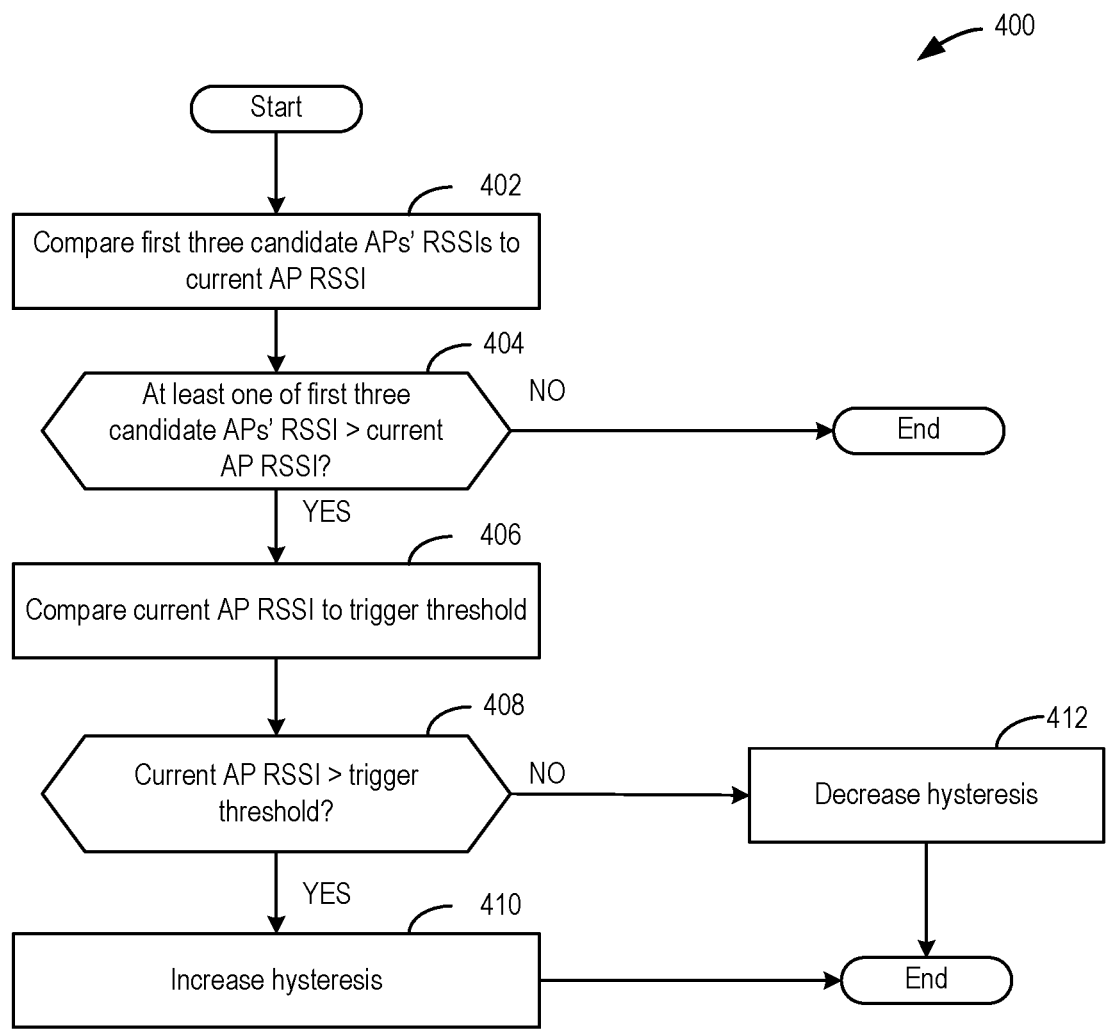
FIG. 4 shows a flow chart illustrating a method for adjusting a hysteresis value as an operation of the method of FIG. 3.

A method 400, as described in FIG. 4, proceeds from operation 306 of the method 300 and illustrates a method for adjusting the hysteresis value. The hysteresis value may be 8 dB and may be initially preset as determined by manufacturers of the WLAN chip or during configuration of the wireless network, for example. As briefly described in FIG. 3, the hysteresis value may be adjusted to control roaming of the Wi-Fi STA while the Wi-Fi STA is mobile and/or when the Wi-Fi STA is stationary and the surrounding environment is changing.

At 402, the method 400 includes comparing RSSI of a first three candidate APs of the reordered list to the RSSI of the connected AP. The reordered list may include three or more than three APs. For example, the first RSSI of the first AP, the second RSSI of the second AP, and the third RSSI of the third AP, as described in FIG. 3, may be compared to the RSSI of the connected AP. As the reordered list lists APs in order of descending RSSIs, the first three candidate APs of the reordered list have the highest RSSI values of the reordered list. In one example, less than three APs may be detected in the network and therefore the reordered list may include less than three APs. The method 400 may thus compare RSSI of the less than three APs of the reordered list to the RSSI of the connected AP. In a further example, the method 400 may include comparing more than the first three candidate APs of the reordered list to the RSSI of the connected AP when the reordered list includes more than three APs.

At 404, the method 400 includes determining if at least one of the first three candidate APs has an RSSI greater than the RSSI of the connected AP. If none of the first three candidate APs of the reordered list has an RSSI greater than the RSSI of the connected AP, the Wi-Fi STA may remain connected to the connected AP and not roam to another AP of the plurality of APs of the wireless network. Thus, although roaming was triggered by the roaming trigger threshold described in FIG. 3, an AP with a stronger connection may not have been identified during scanning.

If at least one of the first three candidate APs has a greater RSSI than the RSSI of the connected AP, the method 400 proceeds to 406, where the method 400 includes comparing the RSSI of the connected AP to a trigger threshold. As described above, the trigger threshold may be an RSSI value initially preset as determined by manufacturers of the WLAN chip or during configuration of the wireless network, manually adjusted by a user, or adjusted based on environmental conditions, for example. The trigger threshold may be different from or the same as the roaming trigger threshold.

At 408, the method 400 includes determining if the RSSI of the connected AP is greater than the trigger threshold. When the RSSI of the connected AP is greater than the trigger threshold, the Wi-Fi STA may refrain from roaming, as a strength of the connection between the connected AP and the Wi-Fi STA may be sufficient for requested data transmission from the Wi-Fi STA to the network via the connected AP. However, as at least one of the first three candidate APs of the reordered list has an RSSI greater than the RSSI of the connected AP, it may be desirable to roam to an AP having a higher RSSI than the RSSI of the connected AP. If the RSSI of the connected AP indicates sufficient signal strength by being greater than the trigger threshold at operation 408, at operation 410, the method 400 includes increasing the hysteresis value.

Increasing the hysteresis value may prevent the Wi-Fi STA from roaming to an AP having an RSSI similar to the RSSI of the connected AP. As the hysteresis value is a threshold RSSI value used to control whether the Wi-Fi STA may roam to a candidate AP from the connected AP, increasing the hysteresis value may allow the Wi-Fi STA to be less selective when roaming. In one example, the hysteresis value may be increased from 2 dB to 10 dB, such that the Wi-Fi STA may not switch from the connected AP to the candidate AP when the candidate AP RSSI is less than 10 dB greater than the RSSI of the connected AP. Instead, the Wi-Fi STA may switch from the connected AP to the candidate AP when the candidate AP RSSI is at least 10 dB greater than the RSSI of the connected AP.

If the RSSI of the connected AP is not greater than the trigger threshold at operation 408, at operation 412, the method 400 includes decreasing the hysteresis value. Decreasing the hysteresis value may allow the Wi-Fi STA to be more selective when roaming. For example, the hysteresis value may be decreased from 10 dB to 2 dB, such that the Wi-Fi STA may switch from the connected AP to the candidate AP when the candidate AP RSSI is within 2 dB of the connected AP RSSI. This may allow the Wi-Fi STA to roam to an AP with a higher RSSI, and thus stronger signal, when the Wi-Fi STA is far from the connected AP and the candidate AP.

In one example, the trigger threshold is −55 dBm, the RSSI of the connected AP is −54 dBm, and the hysteresis value is 3 dB. When the reordered list sequentially includes a first AP as the top AP of the reordered list with an RSSI of −50 dBm, a second AP with an RSSI of −53 dBm, and a third AP with an RSSI of −55 dBm, the hysteresis value may be increased from 3 dB to 8 dB to allow selective roaming of the Wi-Fi STA. When the hysteresis value is 8 dB, the Wi-Fi STA may not roam to the first AP or the second AP, as a difference between the RSSI of the connected AP and each of the first RSSI and the second RSSI is less than the hysteresis value.

In a second example, the trigger threshold is −55 dBm, the RSSI of the connected AP is −65 dBm, and the hysteresis value is 8 dB. When the reordered list sequentially includes a first AP with an RSSI of −60 dBm, a second AP with an RSSI of −63 dBm, and a third AP with an RSSI of −65 dBm, the hysteresis value may be decreased from 8 dB to 3 dB to allow less selective roaming of the Wi-Fi STA. When the hysteresis value is 3 dB, the Wi-Fi STA may roam to the second AP, as a difference between the RSSI of the connected AP the second RSSI is greater than the hysteresis value.

Following adjustment of the hysteresis value, the method 400 may end and return to method 300, which may proceed to operation 308 to scan the reordered list. A reordered scan or a full scan may be implemented to assist in identifying a candidate AP of the wireless network system with a strong signal as coverage levels (e.g., RSSI values) change due to mobility of the Wi-Fi STA, environmental changes, and so on. This may allow rapid, continuous transmission of patient data to the network such that the data may be used by medical personnel for patient care. Further detail is described in FIG. 5 regarding determining whether to implement a reordered scan, thus ending the scan phase earlier than when a full scan is conducted and allowing the Wi-Fi STA to roam to the candidate AP.

A method 500, as described in FIG. 5, proceeds from operation 308 of the method 300 and illustrates a method for determining whether to implement a reordered scan or a full scan of the network using the reordered list of APs. For example, as described above, the reordered scan may include scanning a selection of APs from the reordered list and ending the reordered scan when a candidate AP having an RSSI greater than an RSSI threshold is identified. The full scan may include scanning all APs of the reordered list, and a candidate AP may be identified in the select phase following completion of the full scan.

At 502, the method 500 includes increasing a count of reordered scans by one. In the herein described example, the method 500 may use a configurable reordered scan threshold, where a full scan is implemented after n number of attempted reordered scans, as measured by the count of reordered scans. In one example, the reordered scan threshold may be five, such as when motion of the Wi-Fi STA is not detected. The reordered scan threshold may be two when motion of the Wi-Fi STA is detected. Thus, fewer reordered scans may occur prior to a full scan when the Wi-Fi STA is mobile compared to when the Wi-Fi STA is stationary. The count of reordered scans may begin at zero prior to an attempt to perform a first reordered scan (e.g., following generation of the reordered list at operation 304 of FIG. 3). Following roaming to the candidate AP, the count of reordered scans may be reset to zero.

At 504, the method 500 includes determining if a number of completed reordered scans is less than the reordered scan threshold. For example, the number of completed reordered scans may be measured by the count of reordered scans. If the count of reordered scans is not less than the reordered scan threshold (e.g., the count of reordered scans is greater than the reordered scan threshold), the method 500 includes executing a full scan at 506. The full scan may scan each AP of the reordered list prior to continuing to the select phase to identify a candidate AP.

If, at 504, the number of completed reordered scans is less than the reordered scan threshold, at 508, the method 500 includes determining if at least one candidate AP RSSI is greater than 20 dB below the RSSI threshold. The RSSI threshold may be a sum of the RSSI of the current AP and the hysteresis value (e.g., the hysteresis value adjusted according to the method 400 of FIG. 4). As briefly described in the method 400, the adjusted hysteresis value may be high (e.g., 10 dB) to allow selective roaming of the Wi-Fi STA, and the adjusted hysteresis value may be low (e.g., 2 dB) to allow less selective roaming of the Wi-Fi STA.

If at least one candidate AP RSSI is greater than 20 dB below the RSSI threshold, at 510, the method 500 includes dropping candidate APs with RSSI values greater than 20 dB below the RSSI threshold from the reordered list. An RSSI value greater than 20 dB below the RSSI threshold may provide an insufficient wireless connection between the Wi-Fi STA and the network. Removal of these APs from the reordered list may reduce time and energy used to scan the reordered list, as these APs may be known to have insufficient RSSIs. The 20 dB value may be configurable, for example, APs having RSSI values 15 dB, 25 dB, 30 dB, and so on below the RSSI threshold may be removed from the reordered list.

The method 500 may proceed from operation 510 and from operation 508 (e.g., when it is determined that at least one candidate AP RSSI is not greater than 20 dB below the RSSI threshold) to 512. At 512, the method 500 include returning a first AP scan result (e.g., RSSI) in the reordered list.

At 514, the method 500 includes determining if a candidate AP RSSI is greater than the RSSI threshold. When continuing from operation 512, the candidate AP is the first AP of the reordered list. As described above, the RSSI threshold is the sum of the current AP RSSI and the adjusted hysteresis value. Thus, if a candidate AP RSSI is greater than the RSSI threshold, a wireless connection between the candidate AP and the Wi-Fi STA may result in a stronger connection than the wireless connection between the current AP and the Wi-Fi STA.

If the candidate AP RSSI is not greater than the RSSI threshold, the method 500 proceeds to 516 where the method 500 includes returning an AP scan for the next AP in the reordered list. The next AP thus becomes the candidate AP. This cycle between operation 514 and operation 516 may continue until an AP of the reordered list having an RSSI greater than the RSSI threshold is identified.

For example, the RSSI of the candidate AP may be greater than the RSSI of the connected AP, however the difference may be small enough (e.g., the RSSI of the candidate AP may be 2 dB greater than the RSSI of the connected AP, with an adjusted hysteresis value of 5 dB) that roaming to the candidate AP may result in interruption of data transmission and a non-significant increase in signal strength.

As the RSSI of each of the APs on the reordered list may have changed between the full scan (e.g., operation 302 of method 300) and the scan of the reordered list, the first AP of the reordered list may not have the highest RSSI of the APs of the reordered list. For example, RSSI values may change due to mobility of the Wi-Fi STA and/or changes in the environment. The Wi-Fi STA may be in close proximity to a first AP and far from a second AP and a third AP during the full scan, thus the reordered list orders the plurality of APs as the first AP, the second AP, and the third AP. Prior to the reordered scan of the reordered list, the Wi-Fi STA may move away from the first AP and towards the second AP and the third AP. Thus, the first RSSI of the first AP may decrease and the second RSSI of the second AP and the third RSSI of the third AP may increase. The plurality of APs remain in the order of the reordered list, however the respective RSSIs may have changed. For example, the reordered list based on the full scan may include the first AP with the first RSSI equal to −50 dBm, the second AP with the second RSSI equal to −53 dBm, and the third AP with the third RSSI equal to −55 dBm. When, at operation 502, the first AP is scanned, the first RSSI may be equal to −54 dBm, and thus less than the RSSI threshold when the RSSI of the connected AP is −54 dBm and the adjusted hysteresis value is 3 dB.

When, at 514, it is determined a candidate AP RSSI is greater than the RSSI threshold, at 518, the method 500 include determining if scan termination is allowed. If scan termination is allowed, at 520, the method 500 includes terminating the reordered scan, and the method 500 ends. Thus, the reordered scan includes scanning APs of the reordered list until a candidate AP is identified having an RSSI which may indicate a signal strength between the candidate AP and the Wi-Fi STA greater than the signal strength between the current AP and the Wi-Fi STA. The reordered scan may therefore scan less APs of the reordered list than the full scan, thus reducing a scan time and power draw used to scan. Roaming delay, as described in FIG. 2, may further be reduced, as a duration of the select phase may be reduced due to the Wi-Fi STA having a reduced number of APs to select from.

Scan termination may not be allowed following prior termination of a scan. For example, if during a reordered scan, a candidate AP having an RSSI greater than the RSSI threshold is identified and the reordered scan is terminated, scan termination for a following scan may be disabled. A full scan is thus implemented prior to a reordered scan following a terminated scan. Once the full scan has been implemented, scan termination may be allowed.

If, at 518, scan termination is not allowed, at 522, the method 500 includes determining if all APs of the reordered list have been scanned. For example, multiple APs of the reordered list may be scanned prior to identification of an AP with an RSSI greater than the RSSI threshold. If not all APs of the reordered list have been scanned, at 516, the method 500 includes returning the AP scan for the next AP in the reordered list, as described above. If all APs of the reordered list have been scanned and a candidate AP with an RSSI greater than the RSSI threshold has not been identified, the method 500 returns to operation 502 to increase the count of reordered scans by one.

Continuing with the method 500 from operation 502, if increasing the count of reordered scans by one (e.g., following determination that all APs are scanned) results in the number of completed reordered scans exceeding the reordered scan threshold, the full scan may be executed to identify available APs in the wireless network, which may or may not include APs of the reordered list.

In this way, executing a reordered scan may result in a decreased roaming delay and decreased data loss when switching from a connected AP to a candidate AP due to a shortened reordered list of candidate APs compared to a list of candidate APs generated during a full scan. The Wi-Fi STA may identify and roam to APs of the wireless network having a stronger connection (e.g., greater RSSI), which may allow rapid and uninterrupted transmission of data. Executing a conditional scan, including reordering the list of APs and their respective RSSIs collected during a full scan, and performing a reordered scan may enable more rapid identification of APs with high RSSI values, compared to completing a full scan prior to roaming to a candidate AP. As coverage levels (e.g., RSSI values of the plurality of APs, including the RSSI of the connected AP) change, the methods described herein may allow the Wi-Fi STA to be more or less selective in roaming by adjusting the hysteresis value.

The technical effect of conditionally scanning a wireless network, where conditional scanning includes reordering results of a full scan, adjusting a hysteresis value, and scanning a reordered list to identify a candidate AP to roam to using either a full scan or a reordered scan, is a decrease in roaming delay, reduced data loss, and reduced power draw during roaming of the mobile patient monitor.

The disclosure also provides support for a method for a wireless monitoring system, comprising: performing a scan of a wireless network in a first order to identify a plurality of access points (APs), reordering the plurality of APs into a reordered group of APs based on a received signal strength indicator (RSSI) of each AP of the plurality of APs, and scanning the reordered group in a second order different than the first order to identify a candidate AP of the reordered group to roam to. In a first example of the method, the reordered group includes the plurality of APs in order of descending RSSIs, such that an AP of the plurality of APs with a highest RSSI is listed first in the reordered group and scanned first when scanning the reordered group. In a second example of the method, optionally including the first example, a hysteresis value is adjusted based on a comparison of a connected AP RSSI to a trigger threshold and to a first RSSI of a first AP, a second RSSI of a second AP, and a third RSSI of a third AP of the reordered group. In a third example of the method, optionally including one or both of the first and second examples, the trigger threshold is an RSSI value preset by a manufacturer, manually adjusted by a user, or adjusted based on environmental conditions. In a fourth example of the method, optionally including one or more or each of the first through third examples, the hysteresis value is adjusted when at least one of the first RSSI of the first AP, the second RSSI of the second AP, and the third RSSI of the third AP is greater than the connected AP RSSI. In a fifth example of the method, optionally including one or more or each of the first through fourth examples, the hysteresis value is increased when the connected AP RSSI is greater than the trigger threshold. In a sixth example of the method, optionally including one or more or each of the first through fifth examples, the hysteresis value is decreased when the connected AP RSSI is less than the trigger threshold. In a seventh example of the method, optionally including one or more or each of the first through sixth examples, an RSSI of each AP of the reordered group is sequentially compared to a RSSI threshold following adjustment of the hysteresis value, where the RSSI threshold is a sum of the connected AP RSSI and the hysteresis value. In an eighth example of the method, optionally including one or more or each of the first through seventh examples when the first RSSI of the first AP is greater than the RSSI threshold, the scan is interrupted and interruption of subsequent scans is disabled. In a ninth example of the method, optionally including one or more or each of the first through eighth examples, interruption of subsequent scans is disabled until completion of a full scan of each AP of the wireless network. In a tenth example of the method, optionally including one or more or each of the first through ninth examples when the first RSSI of the first AP is less than or equal to the RSSI threshold, the second RSSI of the second AP is compared to the RSSI threshold. In an eleventh example of the method, optionally including one or more or each of the first through tenth examples, RSSIs of the plurality of APs of the reordered group are sequentially compared to the RSSI threshold until an RSSI of an AP of the reordered group is greater than the RSSI threshold or all APs of the reordered group have been compared to the RSSI threshold.

The disclosure also provides support for a wireless network system, comprising: a network, a plurality of access points (APs) in wireless communication with the network, and a Wi-Fi station (STA) in wireless communication with at least one of the plurality of APs, the Wi-Fi STA configured with computer-readable instructions that when executed cause the Wi-Fi STA to: perform a scan of the network to identify the plurality of APs, reorder a list of the plurality of APs based on a received signal strength indicator (RSSI) of each AP of the plurality of APs, and scan APs of a reordered list of the plurality of APs to identify a candidate AP to roam to. In a first example of the system, the computer-readable instructions are stored on a storage medium of a WLAN card and executed by a processor of the WLAN card. In a second example of the system, optionally including the first example, the Wi-Fi STA is of a mobile medical device. In a third example of the system, optionally including one or both of the first and second examples, each of the plurality of APs broadcasts a beacon at a first frequency, and wherein each of a plurality of beacons broadcast by each of the plurality of APs are received by the STA and recorded as an RSSI value of a respective AP. In a fourth example of the system, optionally including one or more or each of the first through third examples, the RSSI of the AP in wireless communication with the Wi-Fi STA is measured by the Wi-Fi STA. In a fifth example of the system, optionally including one or more or each of the first through fourth examples, the reordered list includes the plurality of APs arranged in order of descending RSSIs, such that an AP of the plurality of APs with a highest RSSI is first on the list and thus scanned first when scanning the reordered list. In a sixth example of the system, optionally including one or more or each of the first through fifth examples, a reordered scan of the reordered list includes identifying candidate APs having an RSSI greater than a value below a sum of a connected AP RSSI and a hysteresis value and removing said candidate APs from the reordered list, wherein further the hysteresis value is adjusted following reordering of the list and is adjusted based on an RSSI of the AP connected to the Wi-Fi STA relative to a trigger threshold and a first RSSI of a first AP, a second RSSI of a second AP, and a third RSSI of a third AP of the reordered list of the plurality of APs, and identifying a candidate AP having an RSSI greater than the sum of the connected AP RSSI and the hysteresis value.

The disclosure also provides support for a method for a Wi-Fi station (STA), comprising: performing a conditional scan, including: performing a scan of a wireless network to identify a plurality of access points (APs), reordering a list of the plurality of APs based on a received signal strength indicator (RSSI) of each AP of the plurality of APs, adjusting a hysteresis value based on a connected AP RSSI and a first RSSI of a first AP, a second RSSI of a second AP, and a third RSSI of a third AP of a reordered list of the plurality of APs, performing a reordered scan of the reordered list to identify a candidate AP of the plurality of APs to roam to, the candidate AP having an RSSI value greater than a sum of the RSSI value of the connected AP and an adjusted hysteresis value, and performing a full scan following a number of reordered scans exceeding a configurable reordered scan threshold or based on environmental conditions, such as scan interruption being disabled.

As used herein, an element or step recited in the singular and preceded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the method and systems, including the best mode, and also to enable a person of ordinary skill in the relevant art to practice the method and systems, including making and using any devices or systems and performing any incorporated methods. The patentable scope of the disclosure is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a wireless monitoring system, comprising:
   performing a scan of a wireless network in a first order to identify a plurality of access points (APs); then
   reordering the plurality of APs into a reordered group of APs based on a received signal strength indicator (RSSI) of each AP of the plurality of APs; and then
   scanning the reordered group in a second order different than the first order to identify a candidate AP of the reordered group to roam to,
   wherein an AP of the plurality of APs with a highest RSSI is listed first in the reordered group, and wherein the AP listed first in the reordered group with the highest RSSI is scanned first during the scanning of the reordered group.

2. The method of claim 1, wherein the reordered group includes the plurality of APs in order of descending RSSIs, and
   wherein the scanning of the reordered group includes scanning multiple APs of the plurality of APs in the reordered group without scanning all of the plurality of APs in the reordered group, and determining one of the multiple APs scanned in the reordered group comprises an RSSI greater than an RSSI threshold; and
   responsive to determining the RSSI of one of the multiple APs scanned in the reordered group is greater than the RSSI threshold, terminating the reordered scan without scanning a remainder of the reordered group.

3. The method of claim 1, wherein a hysteresis value is adjusted based on a comparison of a connected AP RSSI to a trigger threshold and to a first RSSI of a first AP, a second RSSI of a second AP, and a third RSSI of a third AP of the reordered group.

4. The method of claim 3, wherein the trigger threshold is an RSSI value preset by a manufacturer, manually adjusted by a user, or adjusted based on environmental conditions.

5. The method of claim 3, wherein the hysteresis value is adjusted when at least one of the first RSSI of the first AP, the second RSSI of the second AP, and the third RSSI of the third AP is greater than the connected AP RSSI.

6. The method of claim 5, wherein the hysteresis value is increased when the connected AP RSSI is greater than the trigger threshold.

7. The method of claim 5, wherein the hysteresis value is decreased when the connected AP RSSI is less than the trigger threshold.

8. The method of claim 5, wherein an RSSI of each AP of the reordered group is sequentially compared to a RSSI threshold following adjustment of the hysteresis value, and wherein the RSSI threshold is a sum of the connected AP RSSI and the hysteresis value.

9. The method of claim 8, wherein, when the first RSSI of the first AP is greater than the RSSI threshold, the scan is interrupted and interruption of subsequent scans is disabled.

10. The method of claim 9, wherein interruption of subsequent scans is disabled until completion of a full scan of each AP of the wireless network.

11. The method of claim 8, wherein, when the first RSSI of the first AP is less than or equal to the RSSI threshold, the second RSSI of the second AP is compared to the RSSI threshold.

12. The method of claim 8, wherein RSSIs of the plurality of APs of the reordered group are sequentially compared to the RSSI threshold until an RSSI of an AP of the reordered group is greater than the RSSI threshold or all APs of the reordered group have been compared to the RSSI threshold.

13. A wireless network system, comprising:
    a network;
    a plurality of access points (APs) in wireless communication with the network; and
    a Wi-Fi station (STA) in wireless communication with at least one of the plurality of APs, the Wi-Fi STA configured with computer-readable instructions that when executed cause the Wi-Fi STA to:
      perform a scan of the network to identify the plurality of APs, then reorder a list of the plurality of APs based on a received signal strength indicator (RSSI) of each AP of the plurality of APs, and then scan APs of a reordered list of the plurality of APs to identify a candidate AP to roam to,
    wherein an AP of the APs with a highest RSSI is listed first in the reordered list, and wherein the AP listed first in the reordered list with the highest RSSI is scanned first during the scanning of the reordered list.

14. The wireless network system of claim 13, wherein the computer-readable instructions are stored on a storage medium of a WLAN card and executed by a processor of the WLAN card.

15. The wireless network system of claim 13, wherein the Wi-Fi STA is of a mobile medical device.

16. The wireless network system of claim 13, wherein each of the plurality of APs broadcasts a beacon at a first frequency, and wherein each of a plurality of beacons broadcast by each of the plurality of APs are received by the STA and recorded as an RSSI value of a respective AP.

17. The wireless network system of claim 13, wherein the RSSI of the AP in wireless communication with the Wi-Fi STA is measured by the Wi-Fi STA.

18. The wireless network system of claim 13, wherein the reordered list includes the plurality of APs arranged in order of descending RSSIs, such that an AP of the plurality of APs with a highest RSSI is first on the list and thus scanned first when scanning the reordered list.

19. The wireless network system of claim 18, wherein a reordered scan of the reordered list includes identifying candidate APs having an RSSI greater than a value below a sum of a connected AP RSSI and a hysteresis value and removing said candidate APs from the reordered list, and wherein the hysteresis value is adjusted following reordering of the list and is adjusted based on an RSSI of the AP connected to the Wi-Fi STA relative to a trigger threshold and a first RSSI of a first AP, a second RSSI of a second AP, and a third RSSI of a third AP of the reordered list of the plurality of APs, and identifying a candidate AP having an RSSI greater than the sum of the connected AP RSSI and the hysteresis value.

20. A method for a Wi-Fi station (STA), comprising:
performing a conditional scan, including:
    performing a scan of a wireless network to identify a plurality of access points (APs); then
    reordering a list of the plurality of APs based on a received signal strength indicator (RSSI) of each AP of the plurality of APs to form a reordered list, wherein an AP of the plurality of APs with a highest RSSI is listed first in the reordered list;
    adjusting a hysteresis value based on a connected AP RSSI and a first RSSI of a first AP, a second RSSI of a second AP, and a third RSSI of a third AP of the reordered list of the plurality of APs; then
    performing a reordered scan of the reordered list, wherein the AP listed first in the reordered list with the highest RSSI is scanned first during reordered scan of the reordered list;
    identifying a candidate AP of the plurality of APs to roam to based on the reordered scan of the reordered list, the candidate AP having an RSSI value greater than a sum of the RSSI value of the connected AP and an adjusted hysteresis value; and
    performing a full scan following a number of reordered scans exceeding a configurable reordered scan threshold or based on environmental conditions, such as scan interruption being disabled.

* * * * *